United States Patent
Heimbrock

(10) Patent No.: US 6,382,576 B1
(45) Date of Patent: May 7, 2002

(54) CLAMPING APPARATUS

(75) Inventor: Richard H. Heimbrock, Cincinnati, OH (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 09/520,114

(22) Filed: Mar. 7, 2000

Related U.S. Application Data
(60) Provisional application No. 60/138,189, filed on Jun. 8, 1999.

(51) Int. Cl.$^7$ ............................................... A47B 96/00
(52) U.S. Cl. ............................... 248/227.3; 248/226.11; 248/230.4; 294/119.3
(58) Field of Search ........................ 248/229.16, 229.26, 248/219.4, 230.7, 218.4, 124.1, 122.1, 226.1, 227.3, 229.12, 229.13, 231.41, 231.51, 316.4, 316.3, 230.4; 5/615, 715, 503.1, 508.1; 294/119.3

(56) References Cited

U.S. PATENT DOCUMENTS

| | | |
|---|---|---|
| 4,005,844 A | 2/1977 | Richmond |
| 4,190,224 A | 2/1980 | LeBlanc et al. |
| 4,511,158 A * | 4/1985 | Varga et al. ................ 280/292 |
| 4,572,536 A * | 2/1986 | Doughty .............. 280/289 WC |
| 4,815,782 A | 3/1989 | Craig et al. |
| 5,467,543 A * | 11/1995 | Fink et al. .................... 40/538 |
| 5,518,231 A * | 5/1996 | Reddy ................ 294/119.3 X |
| 5,536,056 A * | 7/1996 | Clarke et al. ............ 294/119.3 |
| 5,699,988 A | 12/1997 | Boettger et al. |
| 5,833,291 A | 11/1998 | Haugs |
| 5,987,670 A * | 11/1999 | Sims et al. .................... 5/600 |
| 6,123,217 A * | 9/2000 | Miller ................... 220/592.19 |
| 6,179,260 B1 * | 1/2001 | Ohanian ............... 248/229.16 |

* cited by examiner

Primary Examiner—Ramon O Ramirez
Assistant Examiner—Tan Le
(74) Attorney, Agent, or Firm—Barnes & Thornburg

(57) ABSTRACT

A medical instrument mountable upon a support member includes a bladder that expands against or constricts around the support member when inflated to clamp the instrument to the support member. The medical instrument may include a pressure release valve which deflates the bladder to release the instrument from the support member. The medical instrument may also includes a movable plate which is pressed against the support member when the bladder is inflated to secure the instrument to the support member. The medical instrument may further include a bulb located adjacent to the instrument handle that is squeezed to pump air into the bladder to cause it to expand against or constrict around the support member to secure the instrument to the support member.

17 Claims, 3 Drawing Sheets

CLAMPING APPARATUS

This application claims the benefit of U.S. Provisional Patent Application, Serial No. 60/138,189, filed on Jun. 8, 1999, and entitled "Clamping Apparatus".

BACKGROUND AND SUMMARY OF THE INVENTION

The present invention generally relates to a patient support apparatus—such as a hospital bed or stretcher. More particularly, the present invention relates to a releasable clamping apparatus for clamping a medical device or an instrument to a patient support apparatus.

Medical instruments are often mounted on support members to position such instruments adjacent to a patient lying on a patient support apparatus—such as a stretcher, hospital bed, wheeled chair or an operating table. Such support member could be an IV pole secured to the patient support apparatus or a support rod secured to a side rail of the patient support apparatus. Typically, instruments are clamped to a support member using a vise-like mechanical device that is opened and closed by a screw, lever or a cam.

A quick clamping apparatus in accordance with this invention includes an inflatable member or bladder that expands against or constricts around a support member when inflated to clamp an instrument to the support member. The clamping apparatus may include a pressure release valve which deflates the bladder to release the instrument from the support member.

According to another embodiment of this invention, the clamping apparatus includes a movable plate which is pressed against the support member when the bladder is inflated to secure the instrument to the support member.

According to still another embodiment of this invention, the clamping apparatus includes a pump, such as a bulb, that is squeezed to pump air into the bladder to cause it to expand against or constrict around the support member to secure the instrument to the support member. Such a pump or bulb may be provided adjacent to or as a part of the instrument handle.

A medical apparatus mountable upon a support member in accordance with an embodiment of this invention includes a pneumatically-activated clamp for engaging the support member, a pump for actuating the clamp and a valve for releasing the clamp.

Additional features of the present invention will become apparent to those skilled in the art upon a consideration of the following detailed description of the preferred embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
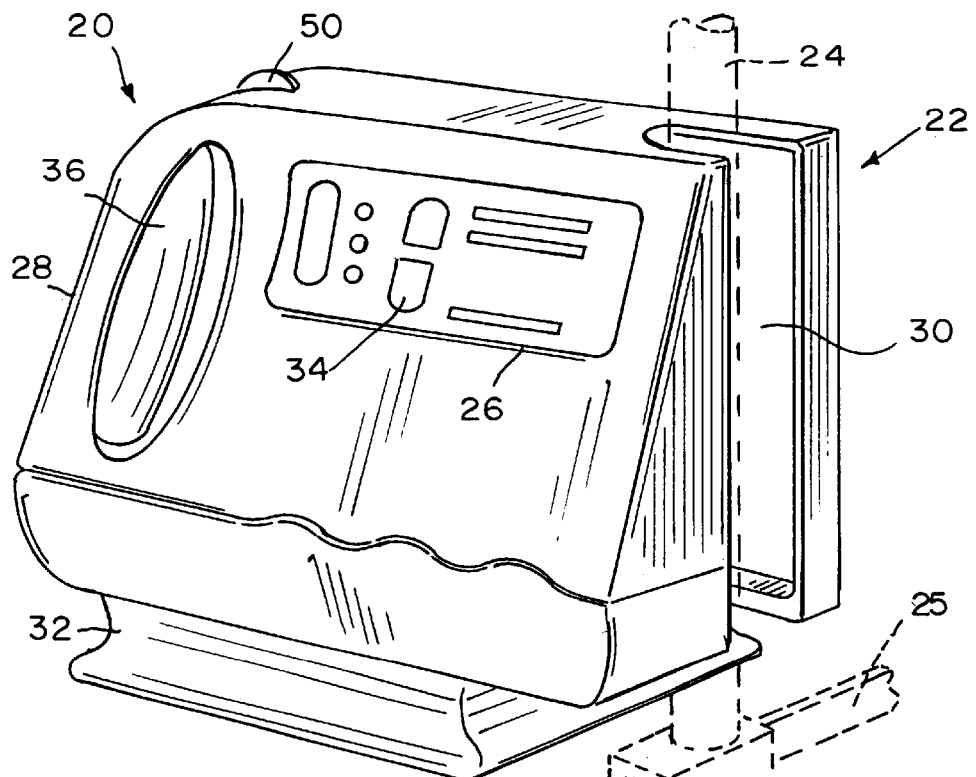
FIG. 1 is a perspective view of a controller including a quick clamping apparatus in accordance with this invention for clamping the controller to a support member, such as an IV pole of a patient support apparatus, the controller having an elongated slot for receiving the support member.
Figure 2:
FIG. 2 is a perspective view similar to FIG. 1, showing an air bulb inside the handle grip of the controller that is squeezed to pump air into an air bladder located inside the elongated slot, the air bladder when inflated constricts around the support member to secure the controller to the support member, the clamping apparatus includes a release button located on the handle grip for releasing the pressure in the air bladder to free the instrument from the support member.
Figure 2:
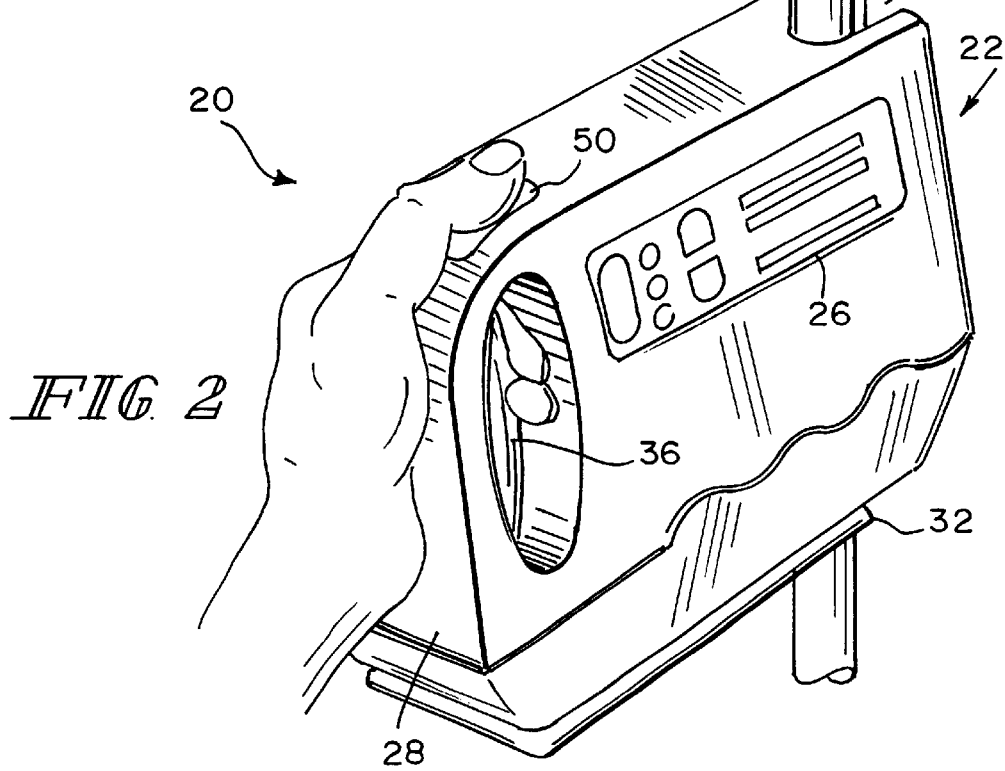
Figure 3:
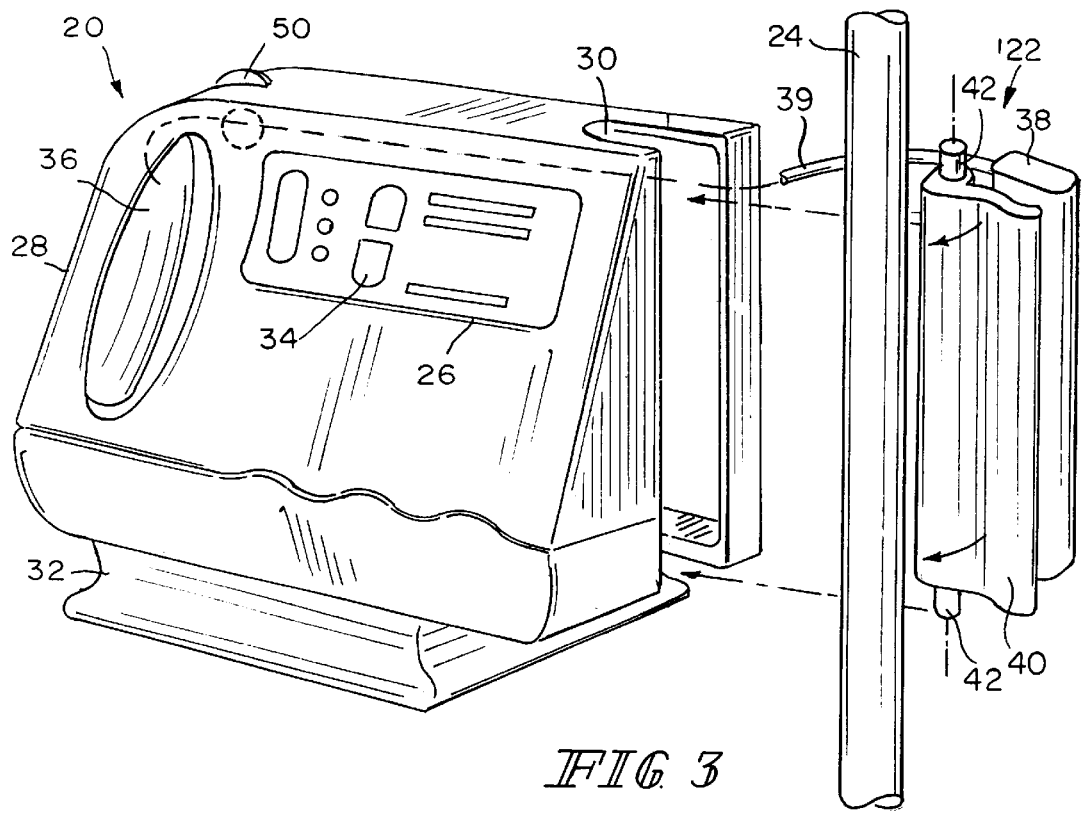
FIG. 3 is a partially-exploded view similar to FIGS. 1 and 2, showing a pivotally mounted plate that is pressed against the support member when the air bladder is inflated to se he controller to the support member.

As shown in FIGS. 1–4, a controller 20 includes a quick clamping apparatus 22 in accordance with the present invention for securing the controller 20 to a support member 24. The support member 24 could be an IV pole secured to a patient support apparatus or a support rod secured to a side element 25 of the patient support apparatus. The controller 20 includes a display and control panel 26, a handle grip 28, an elongated slot 30 for receiving the support member 24, and a perimetrical groove 32 for storing unused power cord. Illustratively, the controller 20 is AC powered with a DC backup, and is used in conjunction with a patient warming system (not shown). The patient warming system includes one or more heating pads, which are plugged into the controller 20 for regulating the temperature of a patient lying on a patient support surface—such as a stretcher, hospital bed or an operating table. A preset temperature is entered into the controller 20 by using a key pad 34. Control circuits included in the controller 20 regulate the current flowing into the heating pads to maintain the temperature of the heating pads at or near the preset temperature in response to the output of sensors included in the heating pads. Although the clamping apparatus 22 is used for supporting a controller of a patient warming system, it may very well be used for supporting any other instrument adjacent to a patient lying on the patient support surface.

Figure 4:
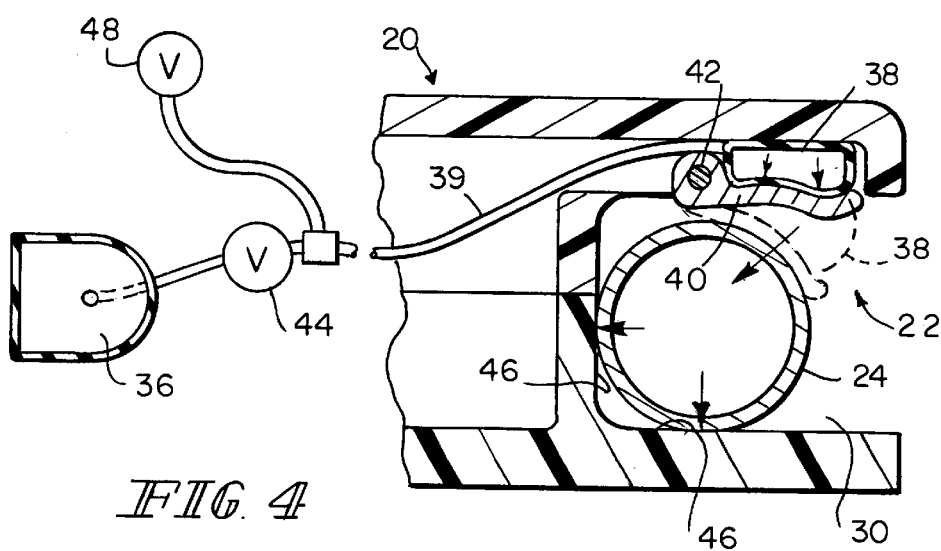
FIG. 4 is a cross sectional view of the clamping apparatus of FIGS. 1–3, schematically showing a non-return valve for preventing air from escaping the air bladder during pumping operation, and a release valve coupled to the air bladder for venting the air bladder to the atmosphere in response to the operation of the release button to free the instrument from the support member.

The clamping apparatus 22 includes a pump, such as an air bulb 36, located adjacent to or as a part of the handle grip 28 which when squeezed pumps air into an air bladder 38 positioned inside the elongated slot 30 through a conduit 39. When inflated, the air bladder 38 causes a plate 40, pivotally mounted inside the elongated slot 30 by pivot pins 42, to press against the support member 24 as shown in phantom in FIG. 4. A non-return valve 44 coupled to the conduit 39 prevents the air in the air bladder 38 from escaping during pumping operation. The support member 24 is squeezed between the pivotally-mounted plate 40 and an interior wall 46 of the elongated slot 30 in the controller 20 to firmly secure the controller 20 to the support member 24. As schematically shown in FIG. 4, the clamping apparatus 22 further includes a release valve 48 coupled to the air bladder 38 for venting the air bladder 38 to the atmosphere in response to the operation of a pressure-release button 50 located on the handle grip 28 to release the controller 20 from the support member 24. Although air is used as a pressure medium in the particular embodiment described, it may very well be any other suitable medium—such as liquid.

Figure 5:
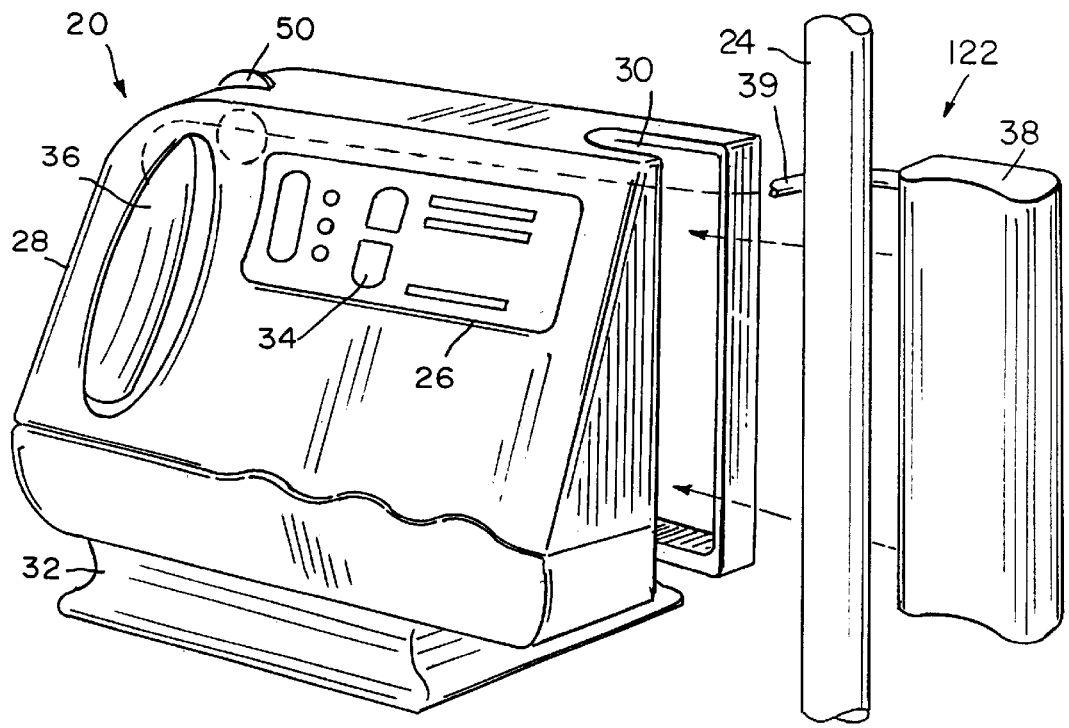
FIGS. 5 and 6 are views similar to FIGS. 3 and 4, showing another embodiment of the present invention, in this embodiment the pivotally-mounted plate is eliminated and the air bladder located inside the elongated slot presses the support member against the inside wall of the elongated slot when inflated to secure the controller to the support member.
Figure 6:
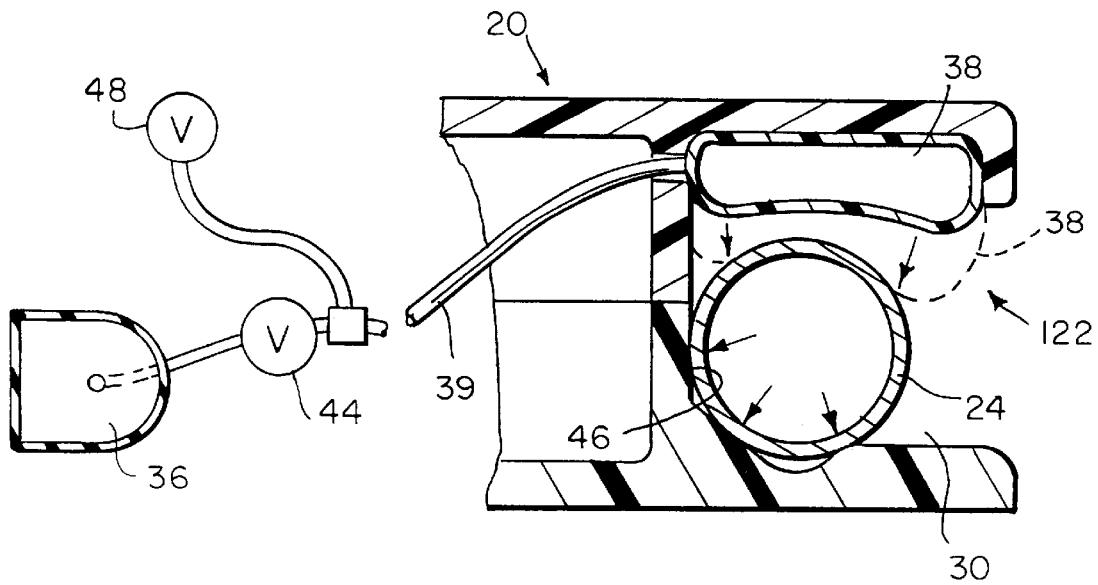

FIGS. 5 and 6 show another embodiment 122 of the clamping apparatus 22 of FIGS. 1–4. Like parts in the two embodiments 22 and 122 are identified by the same reference numerals. In the embodiment 122, the air bladder 38 constricts around the support member 24 when inflated. The support member 24 is squeezed between the air bladder 38 and the wall 46 of the slot 30 in the controller 20 to secure the controller 20 to the support member 24. The pivotally-mounted plate 40 is eliminated in the embodiment 122.

Although the present invention has been described in detail with reference to certain preferred embodiments, variations and modifications exist within the scope and spirit of the present invention as described above.

What is claimed is:

1. An apparatus for removably clamping and supporting a device on a vertical support member comprising:
    a wall configured to be coupled to the device and defining an opening for receiving the vertical support member,
    an inflatable member located in the opening, and
    a conduit communicating with the inflatable member to deliver a pressure medium thereto, and expand the inflatable member in size to engage and wedge the vertical support member against the wall to releasably support the device on the vertical support member with sufficient force to prevent the device from sliding with respect to the vertical support member whereby the device is adapted to be supported from the support member in a cantilevered fashion and said device is adapted to be repositioned along said support member.

2. The apparatus of claim 1, further including a bulb coupled to the conduit which when squeezed delivers pressurized medium to the inflatable member to secure the device to the support member.

3. The apparatus of claim 2, wherein the device includes a handle grip, and wherein the bulb is located adjacent to the handle grip.

4. The apparatus of claim 1, further including a non-return valve coupled to the conduit to prevent the pressurized medium from escaping the inflatable member.

5. The apparatus of claim 1, further including a release valve coupled to the inflatable member to vent the pressurized medium in the inflatable member to the atmosphere in response to the operation of a pressure release button to release the device from the support member.

6. The apparatus of claim 5, wherein the device includes a handle grip, and wherein the pressure release button is located on the handle grip.

7. The apparatus of claim 1, wherein the device is a medical device.

8. The apparatus of claim 7, wherein the medical device is an electric controller which is AC powered with a DC backup.

9. The apparatus of claim 7, wherein the support member is an IV pole secured to a patient support apparatus.

10. The apparatus of claim 7, wherein the support member is a support rod secured to a siderail of a patient support apparatus.

11. An apparatus for removably clamping a device to a support member comprising:
    a wall configured to be coupled to the device and defining an opening for receiving the support member,
    an inflatable member located in the opening,
    a conduit communicating with the inflatable member to deliver a pressure medium thereto, and expand the inflatable member in size to engage and wedge the support member against the wall to releasably support the device on the support member, and
    a plate movably mounted in the opening, wherein expansion of the inflatable member presses the movable plate against the support member to secure the device to the support member.

12. An apparatus for removably clamping a device to a support member, the device having an opening for receiving the support member, the clamping apparatus comprising:
    an inflatable member located in the opening,
    a conduit communicating with the inflatable member to deliver a pressure medium thereto, and expand the inflatable member to engage the support member to releasably secure the device to the support member, and
    a movable plate, wherein expansion of the inflatable member presses the movable plate against the support member to secure the device to the support member,
    wherein the plate is pivotally mounted inside the opening by a pivot pin coupled to the device.

13. An apparatus for removably clamping and supporting a medical device on a vertical support member, the medical device having an opening for receiving the vertical support member, the clamping apparatus comprising:
    an inflatable member located in the opening,
    a conduit communicating with the inflatable member to deliver a pressure medium thereto, and expand the inflatable member to engage the vertical support member to releasably support the medical device on the support member with sufficient force to prevent the device from sliding with respect to the vertical support member whereby the device is adapted to be supported from the support member in a cantilevered fashion and said device is adapted to be repositioned along said support member,
    wherein the medical device is an electric controller which is AC powered with a DC backup, and
    wherein the controller includes a display, a control panel, a handle grip, an elongated slot for receiving the support member and a perimetrical groove for storing unused power cord.

14. An apparatus mountable upon and supported by a vertical support member, the apparatus including a wall defining an opening for receiving the vertical support member, a pneumatically-activated clamp located in the opening for engaging and wedging the vertical support member against the wall to releasably support the apparatus on the vertical support member with sufficient force to prevent the apparatus from sliding with respect to the vertical support member whereby the device is adapted to be supported from the support member in a cantilevered fashion and said device is adapted to be repositioned along said support member, a pump for actuating the clamp and a valve for releasing the clamp.

15. An apparatus mountable upon a support member, the apparatus including a wall defining an opening for receiving the support member, a pneumatically-activated clamp located in the opening for engaging and wedging the support member against the wall to releasably support the apparatus on the support member, a pump for actuating the clamp, a valve for releasing the clamp and a plate movably mounted in the opening, wherein the pneumatically-activated clamp includes a bladder, and wherein actuation of the pump expands the bladder in size to press the movable plate against the support member, and secure the apparatus to the support member.

16. The apparatus of claim 15, wherein the pump includes a bulb coupled to the bladder which when squeezed delivers pressurized medium to the bladder to secure the apparatus to the support member.

17. The apparatus of claim 16, wherein the apparatus includes a handle, and wherein the bulb is located adjacent to the handle.

* * * * *